(12) United States Patent
Abouabdellah et al.

(10) Patent No.: US 7,696,374 B2
(45) Date of Patent: Apr. 13, 2010

(54) ARYLALKLCARBAMATE DERIVATIVES, PREPARATION METHOD THEREOF AND USE OF SAME IN THERAPEUTICS

(75) Inventors: Ahmed Abouabdellah, Thiais (FR); Antonio Almario Garcia, Paris (FR)

(73) Assignee: Sanofi-Aventis, Paris (FR)

( * ) Notice: Subject to any disclaimer, the term of this patent is extended or adjusted under 35 U.S.C. 154(b) by 347 days.

(21) Appl. No.: 11/395,942

(22) Filed: Mar. 31, 2006

(65) Prior Publication Data

US 2006/0223805 A1    Oct. 5, 2006

Related U.S. Application Data

(63) Continuation of application No. PCT/FR2004/002486, filed on Oct. 1, 2004.

(30) Foreign Application Priority Data

Oct. 3, 2003    (FR) .................................. 03 11615

(51) Int. Cl.
*C07C 269/00*    (2006.01)
*A01N 47/10*    (2006.01)
(52) U.S. Cl. ...................... 560/157; 514/478; 514/561; 514/214.01; 544/208; 544/237
(58) Field of Classification Search ................. 514/214, 514/478, 561; 544/208, 237; 546/335; 558/410; 560/24, 157
See application file for complete search history.

(56) References Cited

U.S. PATENT DOCUMENTS

| 2,954,395 | A | 9/1960 | Shapiro et al. |
| 3,600,427 | A | 8/1971 | Verbiscar et al. |
| 5,112,859 | A | 5/1992 | Commons et al. |
| 5,705,504 | A | 1/1998 | Carceller et al. |
| 5,756,507 | A | 5/1998 | Goulet et al. |

FOREIGN PATENT DOCUMENTS

| EP | 0340709 | 11/1989 |
| EP | 0428385 | 5/1991 |
| EP | 0902014 | 3/1999 |
| GB | 1190545 | 5/1970 |
| JP | 49017572 | 5/1974 |
| JP | 49031093 | 8/1974 |
| JP | 49031094 | 8/1974 |
| JP | 49039815 | 10/1974 |
| JP | 50019608 | 7/1975 |
| JP | 53001333 | 1/1978 |
| WO | WO96/31487 | 10/1996 |
| WO | WO97/24343 | 7/1997 |
| WO | WO02/32900 | 4/2002 |
| WO | WO03/065989 | 8/2003 |
| WO | WO 2004/043909 | 5/2004 |

OTHER PUBLICATIONS

Marzo et al. FAAH and anandamide; is 2-AG really the odd one out?, 2008, Trends in Pharmacological Sciences, vol. 29, No. 5, pp. 229-233.*
Batkai, S. et al. Endocannabinoids Acting at Cannabinoid-1 Recepteros Regulate Cardivascular Function in Hypertension, Oct. 2004, Circulation, Journal of the American Heart Association, pp. 1996-2002.*
Boger, D. et al., Exceptionally potent inhibitors of fatty acid amide hydrolase: The enzyme responsible for degradation of endogenous oleamide and anandamide, 2000, PNAS, vol. 97, No. 10, pp. 5044-5049.*
Deutsch, D. et al., Production and physiological Actions of Anandamide in the Vasculature of the Rat Kidney, 1997, J. Clin. Invest., vol. 100, No. 6, pp. 1538-1546.*
Paylor, B. et al., the potency of the fatty acid amide hydrolase inhibitor URB597 is dependent upon the assay pH, 2006, Pharmacological Research, vol. 54, pp. 481-485.*
Steffens, M. et al., Fatty acid amidohydrolase in human neocortex-activity in epileptic and non-epileptic brain tissue and inhibition by putative endocannabinoids, 2005, Neuroscience Letters, vol. 385, pp. 13-17.*
Ashton, W.T., et. al., Irreversible Enzyme Inhibitors. 198. Diaminodihydro-s-Triazines and Diaminopyrimidines Bearing Substituted (Ureidomethyl)Phenyl Substituents as Reversible Inhibitors of Dihydrofolate Reductase, J. Med. Chem. vol. 16, No. 5, (1973) pp. 453-456.
Chong, J.M., et. al., Preparation of Alkyl tert-Butyl Iminodicarbonates , J. Org. Chem. (1993) vol. 58, No. 25, pp. 7300-7303.
Chong, P.Y., et. al., Multilevel Selectivity in the Mild and High Yielding Chlorosilane-Induced Cleavage of Carbamates to Isocyanates, J. Org. Chem. (1998) vol. 63, No. 23, pp. 8515-8521.
Patonay, T., et. al., Alpha-Haloalkyl Haloformates and Related Compounds 1. A Convenient Synthesis of Carbamates Via Chloromethyl Carbonates, Synthetic Communications, vol. 20, No. 18, pp. 2865-2885(1990).
Comins, D.L., et. al., Asymmetric Pictet-Spengler Synthesis of Tetrahydroisoquinolines. An Enantioselective Synthesis of (-)-Laudanosine, Tetrahedron Letters, vol. 32 No. 26, pp. 2995-2996, (1991).

(Continued)

Primary Examiner—Porfirio Nazaril-Gonzalez
Assistant Examiner—Yate' K Cutliff
(74) Attorney, Agent, or Firm—Balaram Gupta

(57) ABSTRACT

The invention relates to a compound having general formula (I):

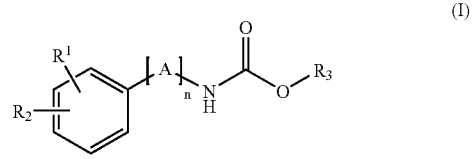

Wherein n, A, $R_1$, $R_2$, and $R_3$ are as defined herein. The invention also relates to methods of preparation of compound of formula (I) as well as its use in therapeutics.

17 Claims, No Drawings

OTHER PUBLICATIONS

Fivush, A.M., et. al., AMEBA: An Acid Sensitive Aldehyde Resin for Solid Phase Synthesis, Tetrahedron Letters, vol. 38, No. 41, pp. 7151-7154 (1997).

Johnson, M.K., Sensitivity and Selectivity of Compounds Interacting with Neuropathy Target Esterase, Biochemical Pharmacology Vol. 37, No. 21, (1988) pp. 4095-4104.

Johnson, M.K., Structure-Activity Relationships for Substrates and Inhibitors of Hen Brain Neurotoxic Esterase, Biochemical Pharmacology, vol. 24, vol. 7, pp. 797-805 (1975).

Jones, G.H., et. al., Inhibitors of Cyclic AMP Phosphodiesterase. 1. Analogues of Cilostamide and Anagrelide, J. Med. Chem. (1987) vol. 30, pp. 295-303.

Jordan, A.M., et. al., Melanocyte-directed Enzyme Prodrug Therapy (MDEPT): Development of second Generation Prodrugs for Targeted Treatment of Malignant Melanoma, Bioorganic & Medicinal Chemistry vol. 9 (2001) pp. 1549-1558.

Khydyrov, D.N., et. al., Synthesis and Investigation of Alpha-Aralkyl Isocyanate Derivatives, Izvestiya Akademii Nauk Turkmenskoi SSR, No. 1, (1989) pp. 75-79—Abstract only.

Kita, Y., et. al., Facile and Efficient Carboalkoxylation and Carboaryloxylation of Amines, J. Org. Chem. vol. 45, No. 22, (1980) pp. 4519-4522.

Kolbezen, M.J., et. al., Insecticidal Activity of Carbamate Cholinesterase Inhibitors, J. Agric. Food Chem. vol. 2, No. 17, (1954) pp. 864-870.

Li, J., et. al., TFA-Sensitive Arylsulfonylthiourea-Assisted Synthesis of N,N-Substituted Guanidines, J. Org. Chem., vol. 68, No. 4, (2003) pp. 1611-1614.

Matsumura, Y., et. al., Electrochemically Induced Hofmann Rearrangement, Tetrahedron Letters, vol. 38, No. 51, pp. 8879-8882 (1997).

Mindl, J., et. al., Cyclization of Substituted Phenyl N-(2-Hydroxybenzyl) Carbamates in Aprotic Solvents. Synthesis of 4H-1,3-Benzoxazin-2(3H)-Ones, Collect. Czech. Chem. Commun, vol. 65, No. 8, 2000 pp. 1262-1272.

Baddeley, G., et. al., Interdependence of Molecular Conformation and Conjugation in Aromatic Ethers Part IV., J. Chem. Soc. (1961) pp. 2516-2519.

Consroe, P., et. al., Brain Cannabinoid Systems as Targets for the Therapy of Neurological Disorders, Neurobiology of Disease, vol. 5, pp. 534-551, (1998).

Iversen, L., et. al., Cannabinoids: A Real Prospect for Pain Relief?, Current Opinion in Pharmacology, (2002), vol. 2, pp. 50-55.

Izzo, A. A., et. al., The Gastrointestinal Pharmacology of Cannabinoids, Current Opinion in Pharmacology, (2001), vol. 1, pp. 597-603.

Jaggar, S. I., et. al., The Anti-Hyperalgesic Actions of the Cannabinoid Anandamide and the Putative CB2 Receptor Agonist Palmitoylethanolamide in Visceral and Somatic Inflammatory Pain, Pain, vol. 76, (1998), pp. 189-199.

Jamshidi, N., et. al., Ananadamide Administration into the Ventromedial Hypothalamus Stimulates Appetite in Rats, British Journal of Pharmacology, (2001), vol. 134, pp. 1151-1154.

Martin, B. R., et. al., Cannabinoid Transamission and Pain Perception, Neurobiology of Disease, vol. 5, pp. 447-461, (1998).

Di Marzo, V., et. al., Leptin-Regulated Endocannabinois are Involved in Maintaining Food Intake, Nature, vol. 410, (2001), pp. 822-825.

Mendelson, W. B., et. al., The Hypnotic Actions of the Fatty Acid Amide, Oleamide, Neuropsychopharmacology, (2001), vol. 25, pp. S36-S39.

Piomelli, D., et. al., The Endocannabinoid System as a Target for Therapeutic Drugs, Trends in Pharmacological Sciences, (2000), vol. 21, pp. 218-224.

Porter, A. C., et. al., The Endocannabinoid Nervous System: Unique Opportunities for Therapeutic Intervention, Pharmacology & Therapeutics, vol. 90, (2001), pp. 45-60.

Smith, P. J. W., et. al., Anandamide Induces Cardiovascular and Respiratory Reflexes Vio Vasosensory Nerves in the Anaesthetized Rat, British Journal of Pharmacology, (2001), vol. 134, pp. 655-663.

Ueda, N., et. al. The Fatty Acid Amide Hydrolase (FAAH), Chemistry and Physics of Lipids, vol. 108, (2000), pp. 107-121.

Van Sickle, M. D., et. al., Cannabinoids Inhibit Emesis Through CB1 Receptors in the Brainstorm of the Ferret, Gastroenterology, vol. 121, pp. 767-774, (2001).

Carley, D. W., et. al., Functional Role for Cannabinoids in Respiratory Stability During Sleep, Sleep, (2002), vol. 25, pp. 391-398.

* cited by examiner

ARYLALKLCARBAMATE DERIVATIVES, PREPARATION METHOD THEREOF AND USE OF SAME IN THERAPEUTICS

CROSS REFERENCE TO RELATED APPLICATIONS

This application is a continuation of International application No. PCT/FR2004/002,486, filed Oct. 1, 2004, which is incorporated herein by reference in its entirety; which claims the benefit of priority of French Patent Application No. 03/11, 615, filed Oct. 3, 2003.

BACKGROUND OF THE INVENTION

Field of the Invention

The invention relates to arylalkylcarbamate derivatives, to the preparation thereof and to the use thereof in therapeutics.

SUMMARY OF THE INVENTION

The compounds of the invention correspond to general formula (I):

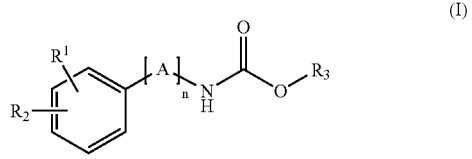

(I)

in which n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

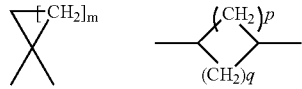

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, a halogen atom, or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents either a 2,2,2-trifluoroethyl group, or a phenyl group optionally substituted with one or more halogen atoms or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl.

In the context of the invention, the compounds of general formula (I) can therefore comprise several groups A which may be identical to or different from one another.

The following compounds are not part of the invention:
2,2,2-trifluoroethyl benzylcarbamate;
2,2,2-trifluoroethyl 4-methoxybenzylcarbamate;
4-nitrophenyl 2-[4-(phenylmethoxy)phenyl]ethylcarbamate;
4-chloro-2-nitrophenyl 2-(4-(chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-dimethyl-3H-imidazo-[4,5-b]pyridin-3-yl)phenyl]ethylcarbamate;
phenyl 2-[4-(3-thienyl)phenyl]propylcarbamate;
phenyl 2-[4-(2-amino-4-thiazolyl)phenyl]ethylcarbamate;
2,3,4,5,6-pentafluorophenyl 4-bromobenzylcarbamate.

DETAILED DESCRIPTION OF THE INVENTION

Among the compounds of general formula (I), a first subgroup of compounds consists of the compounds for which:

n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

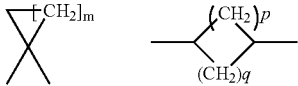

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a halogen atom, or a nitro, hydroxyl, $C_{1-3}$-alkyl or $C_{1-3}$-alkoxy group; and $R_3$ represents either a 2,2,2-trifluoroethyl group, or a phenyl group optionally substituted with one or more halogen atoms, or cyano, nitro, $C_{1-3}$-alkyl, $C_{1-3}$-alkoxy, trifluoromethyl or trifluoromethoxy groups.

The following compounds are not part of the first subgroup of compounds above:

2,2,2-trifluoroethyl 4-methoxybenzylcarbamate;
4-chloro-2-nitrophenyl 2-(4-chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
2,3,4,5,6-pentafluorophenyl 4-bromobenzylcarbamate.

Among the compounds of the general formula (I), a second subgroup of compounds consists of the compounds for which:

n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

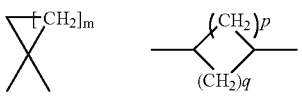

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, or a cyano, $C_{1-3}$-thioalkyl, $C_{1-3}$-fluoroalkyl, $C_{1-3}$-fluoroalkoxy or $C_{1-3}$-fluorothioalkyl group, or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenyl-propoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents either a 2,2,2-trifluoroethyl group, or a phenyl group optionally substituted with one or more halogen atoms or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl.

The following compounds are not part of the second subgroup of compounds above:

2,2,2-trifluoroethyl benzylcarbamate;
4-nitrophenyl 2-[4-(phenylmethoxy)phenyl]ethylcarbamate;
phenyl 2-[4-(2-ethyl-5,7-dimethyl-3H-imidazo[4,5-b]-pyridin-3-yl)phenyl]ethylcarbamate;
phenyl 2-[4-(3-thienyl)phenyl]propylcarbamate;
phenyl 2-[4-(2-amino-4-thiazolyl)phenyl]ethylcarbamate.

Among the compounds of general formula (I), a first family of compounds consists of the compounds for which:

n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

m represents an integer ranging from 1 to 5;

p and q represent integers and are defined such that p+q is a number ranging from 1 to 5;

R₁ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

R₂ represents
a hydrogen atom, a halogen atom,
or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group,
or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, NH₂, NHR₆, NR₆R₇, NHCOR₆, COR₆, CO₂R₆, SO₂R₆, —O—($C_{1-3}$-alkylene)-O—, 4-piperazinyl optionally substituted with a $C_{1-3}$-alkyl or with a benzyl;

R₃ represents
either a 2,2,2-trifluoroethyl group,
or a phenyl group optionally substituted with one or more halogen atoms or cyano, nitro, $C_{1-3}$-alkyl, $C_{1-3}$-alkoxy, trifluoromethyl or trifluoromethoxy groups, and R₆ and R₇ represent, independently of one another, a $C_{1-3}$-alkyl group or a phenyl;

on the condition that when R₃ represents a phenyl group, if A represents a propylene, then R₂ does not represent a thienyl.

The following compounds are not part of the first family of compounds defined above:
2,2,2-trifluoroethyl benzylcarbamate;
2,2,2-trifluoroethyl 4-methoxybenzylcarbamate;
4-nitrophenyl 2-[4-(phenylmethoxy)phenyl]ethylcarbamate;
4-chloro-2-nitrophenyl 2-(4-(chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-dimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate.

Among the compounds of general formula (I), a second family of compounds consists of the compounds for which:
when R₃ represents a 2,2,2-trifluoroethyl group, then n represents an integer between 1 and 6;
A is chosen from one or more groups X, Y and/or Z;
X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;
Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;
Z represents a $C_{3-7}$-cycloalkyl group of formula:

m represents an integer ranging from 1 to 5;
p and q represent integers and are defined such that p+q is a number ranging from 1 to 5;

R₁ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

R₂ represents
a hydrogen atom, a halogen atom,
or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group,
or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, NH₂, NHR₆, NR₆R₇, NHCOR₆, COR₆, CO₂R₆, SO₂R₆, —O—($C_{1-3}$-alkylene)-O—, 4-piperazinyl optionally substituted with a $C_{1-3}$-alkyl or with a benzyl; and R₆ and R₇ represent, independently of one another, a $C_{1-3}$-alkyl group or a phenyl;
when R₃ represents a phenyl group optionally substituted with one or more halogen atoms, or cyano, nitro, $C_{1-3}$-alkyl, $C_{1-3}$-alkoxy, trifluoromethyl or trifluoromethoxy groups, then
n represents an integer between 1 and 6;
A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

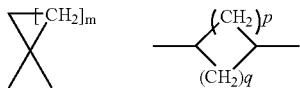

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, a halogen atom, or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group, or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl; and $R_6$ and $R_7$ represent, independently of one another, a $C_{1-3}$-alkyl group or a phenyl.

The following compounds are not part of the second family of compounds defined above:

2,2,2-trifluoroethyl benzylcarbamate;
2,2,2-trifluoroethyl 4-methoxybenzylcarbamate;
4-nitrophenyl 2-[4-(phenylmethoxy)phenyl]ethylcarbamate;
4-chloro-2-nitrophenyl 2-(4-(chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-dimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate.

Among the compounds of general formula (I), a third family of compounds consists of the compounds for which:

n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

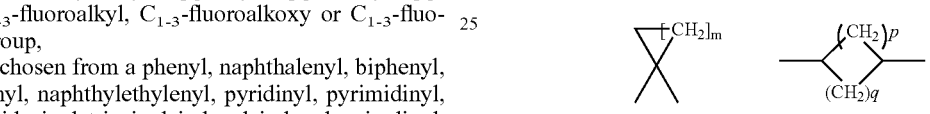

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, a halogen atom, or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group, or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents
either a 2,2,2-trifluoroethyl group,
or a phenyl group optionally substituted with one or more halogen atoms, or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl;
on the condition that
when $R_3$ represents a 2,2,2-trifluoroethyl group,
if A represents a methylene and if $R_1$ represents a hydrogen, then $R_2$ is neither a hydrogen nor a methoxy;
if A represents a methylene and if $R_2$ represents a hydrogen, then $R_1$ is neither a hydrogen nor a methoxy;
when $R_3$ represents a phenyl group,
if A represents a methylene, then neither $R_1$ nor $R_2$ represents a chlorine atom, a methoxy group or a nitro group;
if A represents an ethylene, then neither $R_1$ nor $R_2$ represents a methoxy;
$R_2$ represents neither a 2-ethyl-5,7-dimethyl-3H-imidazo[4,5-b]pyridin-3-yl nor a 2-amino-4-thiazolyl;
if A represents a propylene, then $R_2$ does not represent a 3-thienyl;
when $R_3$ represents a phenyl group substituted with one to five chlorine or fluorine atoms or nitro or cyano groups,
if A represents a methylene, then neither $R_1$ nor $R_2$ represents a methoxy or a bromine atom;
if A represents an ethylene, then neither $R_1$ nor $R_2$ represents a chlorine atom, or a hydroxyl, methyl or methoxy group;
$R_2$ does not represent a phenylmethoxy.

Among the compounds of general formula (I), a fourth family of compounds consists of the compounds for which:
when $R_3$ represents a 2,2,2-trifluoroethyl group, then n represents an integer between 1 and 6;
A is chosen from one or more groups X, Y and/or Z;
X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;
Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;
Z represents a $C_{3-7}$-cycloalkyl group of formula:

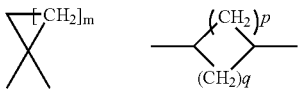

m represents an integer ranging from 1 to 5;
p and q represent integers and are defined such that p+q is a number ranging from 1 to 5;
$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;
$R_2$ represents
a halogen atom
or a cyano, nitro, hydroxyl, $C_{1-3}$-alkyl, $C_{2-3}$-alkoxy, $C_{1-3}$-thioalkyl, $C_{1-3}$-fluoroalkyl, $C_{1-3}$-fluoroalkoxy or $C_{1-3}$-fluorothioalkyl group,
or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl; and $R_6$ and $R_7$ represent, independently of one another, a $C_{1-3}$-alkyl group or a phenyl;
when $R_3$ represents a phenyl group optionally substituted with one or more halogen atoms, or cyano, nitro, $C_{1-3}$-alkyl, $C_{1-3}$-alkoxy, trifluoromethyl or trifluoromethoxy groups, then
n represents an integer between 1 and 6;
A is chosen from one or more groups X, Y and/or Z;
X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;
Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;
Z represents a $C_{3-7}$-cycloalkyl group of formula:

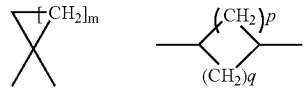

m represents an integer ranging from 1 to 5;
p and q represent integers and are defined such that p+q is a number ranging from 1 to 5;
$R_1$ represents a hydrogen atom, an iodine atom, or a cyano, $C_{2-3}$-alkyl, $C_{2-3}$-alkoxy, $C_{1-3}$-thioalkyl, $C_{1-3}$-fluoroalkyl, $C_{1-3}$-fluoroalkoxy or $C_{1-3}$-fluorothioalkyl group;
$R_2$ represents
a hydrogen atom, an iodine atom,
or a cyano, $C_{2-3}$-alkyl, $C_{2-3}$-alkoxy, $C_{1-3}$-thioalkyl, $C_{1-3}$-fluoroalkyl, $C_{1-3}$-fluoroalkoxy or $C_{1-3}$-fluorothioalkyl group,
or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, furyl, pyrrolyl, imidazolyl, pyrazolyl, oxazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl; and $R_6$ and $R_7$ represent, independently of one another, a $C_{1-3}$-alkyl group or a phenyl.

Among the compounds of general formula (I), a fifth family of compounds consists of the compounds for which:

n represents an integer between 1 and 6;

A is chosen from one or more groups X, Y and/or Z;

X represents a $C_{1-2}$-alkylene group optionally substituted with one or more $C_{1-12}$-alkyl, $C_{3-7}$-cycloalkyl or $C_{3-7}$-cycloalkyl-$_{1-6}$-alkylene groups;

Y represents a $C_2$-alkenylene group optionally substituted with one or more $C_{1-12}$-alkyl, $C_{3-7}$-cycloalkyl or $C_{3-7}$-cycloalkyl-$C_{1-6}$-alkylene groups; or a group —C≡C—;

Z represents a $C_{3-7}$-cycloalkyl group of formula:

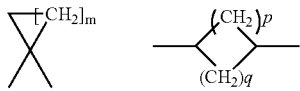

m represents an integer ranging from 1 to 5;

p and q represent integers and are defined such that p+q is a number ranging from 1 to 5;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, or a phenyl or phenyloxy group, this group being optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents either a 2,2,2-trifluoroethyl group, or a phenyl group optionally substituted with one or more halogen atoms, or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl;

2,2,2-trifluoroethyl benzylcarbamate being excluded.

Among the compounds of general formula (I), a sixth family of compounds consists of the compounds for which:

n represents an integer between 1 and 6;

A is a group X;

the groups A being identical to or different from one another when n is an integer between 2 and 6;

X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, a halogen atom, or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy, $C_{1-3}$-fluorothioalkyl group, or a group chosen from a phenyl, naphthalenyl, biphenyl, phenylethylenyl, naphthylethylenyl, pyridinyl, pyrimidinyl, pyrazinyl, pyridazinyl, triazinyl, indanyl, indenyl, quinolinyl, isoquinolinyl, quinazolinyl, quinoxalinyl, phthalazinyl, cinnolinyl, thienyl, furyl, pyrrolyl, imidazolyl, pyrazolyl, oxazolyl, thiazolyl, isoxazolyl, isothiazolyl, thiadiazolyl, oxadiazolyl, triazolyl, benzothienyl, benzofuryl, dibenzofuryl, benzimidazolyl, benzotriazolyl, indolyl, isoindolyl, indazolyl, benzoxazolyl, benzisoxazolyl, benzothiazolyl, benzisothiazolyl, dihydroindolyl, pyrrolopyridinyl, furopyridinyl, thienopyridinyl, imidazopyridinyl, oxazolopyridinyl, thiazolopyridinyl, pyrazolopyridinyl, isoxazolopyridinyl, isothiazolopyridinyl, tetrahydroquinolinyl, tetrahydroisoquinolinyl, phenyloxy, phenylthio, phenylsulfonyl, benzoyl, phenylmethoxy, phenylethoxy, phenylpropoxy, naphthalenyloxy, naphthalenylmethoxy, naphthalenylethoxy, naphthalenylpropoxy, quinolinoxy and isoquinolinoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents either a 2,2,2-trifluoroethyl group, or a phenyl group optionally substituted with one or more halogen atoms, or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl;

on the condition that:

when $R_3$ represents a 2,2,2-trifluoroethyl group and the group -[A]$_n$- represents a —$CH_2$— group, then $R_1$ is other than a hydrogen atom or than a methoxy group;

when $R_3$ represents an optionally substituted phenyl group and the group -[A]$_n$- represents a —$CH_2$—, —$CH_2CH_2$—, —$CH(CH_3)$— or —$CH(CH_3)$—$CH_2$— group;

then $R_1$ is other than a hydrogen or chlorine atom or than a methyl or methoxy group, and $R_2$ is other than a hydrogen atom.

The compounds of general formula (I) can comprise one or more asymmetrical carbons. They can exist in the form of enantiomers or of diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

These salts are advantageously prepared with pharmaceutically acceptable acids, but the salts of other acids useful, for example, for the purification or the isolation of the compounds of formula (I) are also part of the invention. The compounds of general formula (I) can be in the form of hydrates or of solvates, i.e. in the form of associations or of combinations with one or more molecules of water or with a solvent. Such hydrates and solvates are also part of the invention.

In the context of the invention:

- the expression "$C_{t-z}$ where t and z can have the values from 1 to 12" is intended to mean a carbon-based chain that can have from t to z carbon atoms; for example, "$C_{1-3}$" is intended to mean a carbon-based chain which can have from 1 to 3 carbon atoms;
- the term "alkyl" is intended to mean a linear or branched, saturated aliphatic group; for example, a $C_{1-3}$-alkyl group represents a linear or branched carbon-based chain of 1 to 3 carbon atoms, more particularly a methyl, ethyl, propyl or 1-methylethyl;
- the term "alkylene" is intended to mean a linear or branched, saturated divalent alkyl group; for example, a $C_{1-3}$-alkylene group represents a linear or branched divalent carbon-based chain of 1 to 3 carbon atoms, more particularly a methylene, ethylene, 1-methylethylene or propylene;
- the term "cycloalkyl" is intended to mean a cyclic alkyl group; for example, a $C_{3-5}$-cycloalkyl group represents a cyclic carbon-based group of 3 to 5 carbon atoms, more particularly a cyclopropyl, cyclobutyl or cyclopentyl;
- the term "alkenylene" is intended to mean a divalent unsaturated aliphatic group, more particularly an ethylene;
- the term "alkoxy" is intended to mean an —O-alkyl group comprising a linear or branched, saturated aliphatic chain;
- the term "thioalkyl" is intended to mean an —S— alkyl group comprising a linear or branched, saturated aliphatic chain;
- the term "fluoroalkyl" is intended to mean an alkyl group in which one or more hydrogen atoms have been substituted with a fluorine atom;
- the term "fluoroalkoxy" in intended to mean an alkoxy group in which one or more hydrogen atoms have been substituted with a fluorine atom;
- the term "fluorothioalkyl" is intended to mean a thioalkyl group in which one or more hydrogen atoms have been substituted with a fluorine atom;
- the term "halogen atom" is intended to mean a fluorine, a chlorine, a bromine or an iodine.

The compounds of the invention can be prepared according to various methods, illustrated by the schemes which follow.

Thus, a first method (scheme 1) for preparing the compounds of general formula (I) consists in reacting an amine of general formula (II), in which $R_1$, $R_2$, n and A are as defined above, with a carbonate of general formula (III), in which U represents a hydrogen atom or a nitro group and $R_3$ is as defined above, in a solvent such as toluene or dichloroethane, at a temperature of between 0 and 80° C.

Scheme I

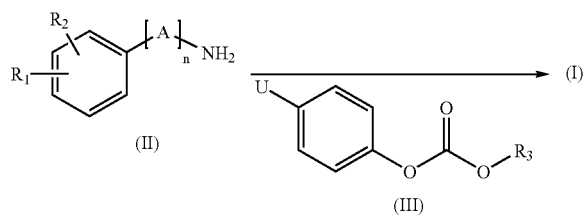

According to a second method, the compounds of general formula (I) for which $R_3$ represents more particularly an optionally substituted phenyl can be prepared by reacting an amine of general formula (II), as defined above, with an aryl chloroformate of general formula (IIIa)

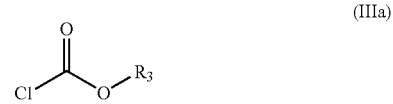

where $R_3$ represents a phenyl group optionally substituted with one or more halogen atoms, or cyano, nitro, $C_{1-3}$-alkyl, $C_{1-3}$-alkoxy, trifluoromethyl or trifluoromethoxy groups, in a solvent such as dichloromethane or dichloroethane in the presence of a base such as triethylamine or diisopropylethylamine, at a temperature of between 0° C. and the reflux temperature of the solvent.

The carbonates of general formula (III) can be prepared according to any method described in the literature, for example by reaction of an alcohol of general formula HOR$_3$ with phenyl chloroformate or para-nitrophenyl chloroformate, in the presence of a base such as triethylamine or diisopropylethylamine.

The compounds of general formulae (II) and (IIIa) are commercially available or described in the literature, or else can be prepared according to methods which are described therein or which are known to those skilled in the art.

When $R_2$ represents a group of aryl or heteroaryl type in a compound of formula (I) or (II), the introduction of $R_2$ onto the phenyl ring can be carried out by reacting a derivative of a compound of general formula (I) or (II) in which the phenyl ring bears a chlorine, bromine or iodine atom or a triflate group, in the position where it is desired to introduce $R_2$, with an aryl- or heteroaryl boronic acid derivative in accordance with the Suzuki reaction conditions (*Chem. Rev.* (1995), 95, 2457-2483; *Angew. Chem. Int.*, Ed. (1999), 38, 3387-3388), or with an aryl- or heteroaryl trialkyltin derivative in accordance with the Stille reaction conditions (*Angew. Chem. Int. Ed. Engl.* (1986), 25, 508-524).

The following examples illustrate the preparation of some compounds of the invention. They are not limiting and merely illustrate the invention. The NMR spectra and/or the LC-MS (Liquid Chromatography coupled to Mass Spectroscopy) confirm the structures and the purities of the compounds obtained.

Mp (° C.) represents the melting point in degrees Celsius.

The numbers indicated between parentheses in the titles of the examples correspond to those of the 1st column of the table hereinafter.

The IUPAC nomenclature (International Union of Pure and Applied Chemistry) was used to name the compounds in the following examples. For example, for the biphenyl group, the following numbering was observed:

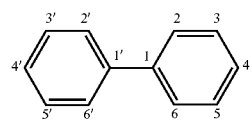

EXAMPLE 1

Compound No. 1

2,2,2-Trifluoroethyl 1,1'-biphenyl-4-ylmethylcarbamate 0.119 ml (1.64 mmol) of 2,2,2-trifluoroethanol and 0.306 ml (1.49 mmol) of N,N-diisopropylethylamine are added, dropwise and at ambient temperature, to a solution of 0.3 g (1.49 mmol) of para-nitrophenyl chloroformate in 15 ml of methylene chloride. The mixture is stirred at ambient temperature for 2 h, and then 0.275 g (1.5 mmol) of 4-phenylbenzylamine is added. N,N-Diisopropylethylamine is subsequently added, dropwise and at ambient temperature, until the precipitate which has formed disappears. The transparent solution thus obtained is stirred at ambient temperature for 1 h. The reaction medium is diluted with a further 10 ml of methylene chloride and washing is carried out with a saturated aqueous ammonium chloride solution and with a saturated aqueous sodium chloride solution. The phases are separated and the organic phase is dried over sodium sulfate. The product is filtered, the filtrate is concentrated under reduced pressure and the residue is purified by silica gel chromatography with methylene chloride.

0.215 g of white solid is obtained.

LC-MS: 310

Mp (° C.): 123-125° C.

$^1$H NMR (DMSO-$d_6$) δ(ppm): 8.25 (t, 1H); 7.75-7.30 (m, 9H); 4.65 (q, 2H); 4.25 (d, 2H).

EXAMPLE 2

Compound No. 19

2,2,2-Trifluoroethyl 2-(1,1'-biphenyl-4-yl)ethylcarbamate

The procedure is carried out in a manner similar to Example 1, replacing the 4-phenylbenzylamine with 2-(4-biphenyl)ethylamine.

0.311 g of white solid is obtained.

LC-MS: 324

Mp (° C.): 79-81° C.

$^1$H NMR (DMSO-$d_6$) δ(ppm): 7.80-7.20 (m, 10H); 4.65 (q, 2H); 3.30 (m, 2H); 2.75 (t, 2H).

EXAMPLE 3

Compound No. 10

2,2,2-Trifluoroethyl 4-phenyloxybenzylcarbamate

The procedure is carried out in a manner similar to Example 1, replacing the 4-phenylbenzylamine with 4-phenyloxybenzylamine.

0.252 g of white solid is obtained.

LC-MS: 326

Mp (° C.): 145-148° C.

$^1$HNMR(DMSO-$d_6$) δ(ppm): 8.15 (t, 1H); 7.40-6.90 (m, 9H); 4.65 (q, 2H); 4.20 (d, 2H).

EXAMPLE 4

Compound No. 3

4-Fluorophenyl 1,1'-biphenyl-4-ylmethylcarbamate 0.069 ml (0.522 mmol) of 4-fluorophenyl chloroformate and 0.149 ml (0.82 mmol) of N,N-diisopropylethylamine are added, dropwise and at ambient temperature, to a solution of 0.107 g (0.58 mmol) of 4-phenylbenzylamine in 4 ml of methylene chloride. The mixture is stirred at ambient temperature for 1 h. The reaction medium is diluted with a further 2 ml of methylene chloride and washed with a saturated aqueous ammonium chloride solution and with a saturated aqueous sodium chloride solution. The phases are separated and the organic phase is filtered through a hydrophobic sintered glass funnel. The filtrate is concentrated under reduced pressure and the solid residue is washed with 5 ml of diisopropyl ether.

0.136 g of white solid is obtained.

LC-MS: 322

Mp (° C.): 155-157° C.

$^1$H NMR(DMSO-$d_6$) δ(ppm): 8.30 (t, 1H); 7.70-7.10 (m, 13H); 4.30 (d, 2H).

EXAMPLE 5

Compound No. 26

4-Methylphenyl 2-(1,1'-biphenyl-4-yl)ethylcarbamate

The procedure is carried out in a manner similar to Example 4, replacing the 4-phenylbenzylamine with 2-(4-biphenyl)ethylamine and the 4-fluorophenyl chloroformate with 4-methylphenyl chloroformate.

0.126 g of white solid is obtained.

LC-MS: 332

Mp (° C.): 172-174° C.

$^1$H NMR(DMSO-$d_6$) δ(ppm): 7.75 (t, 1H); 7.70-7.30 (m, 9H); 7.10 (d, 2H); 6.90 (d, 2H); 3.30 (m, 2H); 2.80 (t, 2H); 2.25 (s, 3H).

EXAMPLE 6

Compound No. 16

4-Methoxyphenyl 4-phenyloxybenzylcarbamate

The procedure is carried out in a manner similar to Example 4, replacing the 4-phenylbenzylamine with 4-phenyloxybenzylamine and the 4-fluorophenyl chloroformate with 4-methoxyphenyl chloroformate.

0.137 g of white solid is obtained.

LC-MS: 350

Mp (° C.): 89-91° C.

$^1$H NMR(DMSO-$d_6$) δ(ppm): 8.20 (t, 1H); 7.45-7.25 (m, 4H); 7.20-6.80 (m, 9H); 4.25 (d, 2H); 3.75 (s, 3H).

The following table illustrates the chemical structures and the physical properties of some compounds according to the invention. In this table, "n.d." signifies that the melting point could not be determined (product in the form of a gum, for example).

TABLE

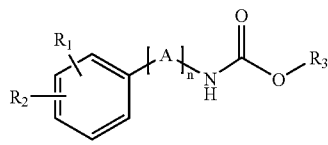

(I)

| No. | $[A]_n$ | $R_1$ | $R_2$ | $R_3$ | Mp (°C.) |
|---|---|---|---|---|---|
| 1. | $CH_2$ | H | 4-phenyl | $CH_2CF_3$ | 123-125 |
| 2. | $CH_2$ | H | 4-phenyl | phenyl | 158-162 |
| 3. | $CH_2$ | H | 4-phenyl | 4-F-phenyl | 155-157 |
| 4. | $CH_2$ | H | 4-phenyl | 2-Cl-phenyl | 128-130 |
| 5. | $CH_2$ | H | 4-phenyl | 4-Cl-phenyl | 161-164 |
| 6. | $CH_2$ | H | 4-phenyl | 2-$CH_3$O-phenyl | 186-188 |
| 7. | $CH_2$ | H | 4-phenyl | 4-$CH_3$O-phenyl | 153-156 |
| 8. | $CH_2$ | H | 4-phenyl | 4-$CH_3$-phenyl | 153-155 |
| 9. | $CH_2$ | H | 4-phenyl | 3-$CF_3$-phenyl | n.d. |
| 10. | $CH_2$ | H | 4-phenyloxy | $CH_2CF_3$ | 145-148 |
| 11. | $CH_2$ | H | 4-phenyloxy | phenyl | 99-101 |
| 12. | $CH_2$ | H | 4-phenyloxy | 4-F-phenyl | 82-84 |
| 13. | $CH_2$ | H | 4-phenyloxy | 2-Cl-phenyl | 106-109 |
| 14. | $CH_2$ | H | 4-phenyloxy | 4-Cl-phenyl | 90-93 |
| 15. | $CH_2$ | H | 4-phenyloxy | 2-$CH_3$O-phenyl | 84-86 |
| 16. | $CH_2$ | H | 4-phenyloxy | 4-$CH_3$O-phenyl | 89-91 |
| 17. | $CH_2$ | H | 4-phenyloxy | 4-$CH_3$-phenyl | 105-107 |
| 18. | $CH_2$ | H | 4-phenyloxy | 3-$CF_3$-phenyl | n.d. |
| 19. | $CH_2CH_2$ | H | 4-phenyl | $CH_2CF_3$ | 79-81 |
| 20. | $CH_2CH_2$ | H | 4-phenyl | phenyl | 150-152 |
| 21. | $CH_2CH_2$ | H | 4-phenyl | 4-F-phenyl | 160-163 |
| 22. | $CH_2CH_2$ | H | 4-phenyl | 2-Cl-phenyl | 131-133 |
| 23. | $CH_2CH_2$ | H | 4-phenyl | 4-Cl-phenyl | 167-169 |
| 24. | $CH_2CH_2$ | H | 4-phenyl | 2-$CH_3$O-phenyl | 116-119 |
| 25. | $CH_2CH_2$ | H | 4-phenyl | 4-$CH_3$O-phenyl | 158-160 |
| 26. | $CH_2CH_2$ | H | 4-phenyl | 4-$CH_3$-phenyl | 172-174 |
| 27. | $CH_2CH_2$ | H | 4-phenyl | 3-$CF_3$-phenyl | 132-135 |
| 28. | $CH_2CH_2CH_2$ | H | H | phenyl | 62-65 |
| 29. | $CH_2CH_2CH_2$ | H | H | 4-F-phenyl | 61-63 |
| 30. | $CH_2CH_2CH_2$ | H | H | 4-Cl-phenyl | 53-56 |
| 31. | $CH_2CH_2CH_2$ | H | H | 4-$CH_3$-phenyl | 79-81 |
| 32. | $CH_2CH_2CH_2CH_2$ | H | H | phenyl | 76-78 |
| 33. | $CH_2CH_2CH_2CH_2$ | H | H | 4-F-phenyl | 91-93 |
| 34. | $CH_2CH_2CH_2CH_2$ | H | H | 4-Cl-phenyl | 95-97 |
| 35. | $CH_2CH_2CH_2CH_2$ | H | H | 4-$CH_3$-phenyl | 91-93 |

The compounds of the invention were subjected to pharmacological assays to determine their inhibitory effect on the FAAH enzyme (fatty acid amido hydrolase).

The inhibitory activity was demonstrated in a radioenzymatic assay based on measuring the product of hydrolysis (ethanolamine [1-$^3$H]) of anandamide [ethanolamine 1-$^3$H] by FAAH (*Life Sciences* (1995), 56, 1999-2005) and (*Journal of Pharmacology and Experimented Therapeutics* (1997), 283, 729-734). Thus, mouse brains (minus the cerebellum) are removed and conserved at −80° C. Membrane homogenates are prepared extemporaneously by homogenization of the tissues with a Polytron in a 10 mM Tris-HCl buffer (pH 8.0) containing 150 mM NaCl and 1 mM EDTA. The enzymatic reaction is subsequently carried out in 70 μl of buffer containing fatty acid-free bovine serum albumin (1 mg/ml). The compounds tested, at various concentrations, anandamide [ethanolamine 1-$^3$H] (specific activity of 15-20 Ci/mmol) diluted to 10 μM with cold anandamide, and the membrane preparation (400 μg of frozen tissue per assay) are added successively. After 15 minutes at 25° C., the enzymatic reaction is stopped by adding 140 μl of chloroform/methanol (2:1). The mixture is stirred for 10 minutes and then centrifuged for 15 minutes at 3500 g. An aliquot (30 μl) of the aqueous phase containing the ethanolamine [1-$^3$H] is counted by liquid scintillation.

Under these conditions, the most active compounds of the invention exhibit $IC_{50}$ values (concentration that inhibits 50% of the control enzymatic activity of FAAH) between 0.001 and 1 μM.

It therefore appears that the compounds according to the invention have an inhibitory activity on the FAAH enzyme.

The FAAH enzyme (*Chemistry and Physics of Lipids*, (2000), 108, 107-121) catalyses the hydrolysis of endogenous derivatives of amides and of esters of various fatty acids such as N-arachidonoylethanolamine (anandamide), N-palmitoylethanolamine, N-oleylethanolamine, oleamide or 2-arachidonoylglycerol. These derivatives exert various pharmacological activities by interacting, inter alia, with cannabinoid and vanilloid receptors.

The compounds of the invention block this degradation pathway and increase the tissue content of these endogenous substances. They can be used in this respect in the prevention and treatment of pathologies in which endogenous cannabinoids and/or any other substrates metabolized by the FAAH enzyme are involved.

Mention may, for example, be made of the following diseases and conditions:

pain, in particular acute or chronic pain of neurogenic type: migraine, neuropathic pain including the forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain:

dizziness, vomiting, nausea, in particular those subsequent to chemotherapy;

eating disorders, in particular anorexia and cachexia of various natures;

neurological and psychiatric pathologies: shaking, dyskinesia, dystonia, spasticity, obsessive compulsive disorders, Tourette's syndrome, all forms of depression and anxiety of any nature and origin, mood disorders, psychoses;

acute and chronic neurodegenerative diseases: Parkinson's disease, Alzheimer's disease, senile dementia, Huntington's chorea, lesions related to cerebral ischemia and to cranial and medullary traumas; epilepsy;

sleeping disorders, including sleep apnea;

cardiovascular diseases, in particular hypertension, cardiac arrhythmias, arteriosclerosis, heart attack, cardiac ischemias;

renal ischemia;

cancers: benign skin tumors, papillomas and brain tumors, prostate tumors, brain tumors (glioblastomas, medulloepitheliomas, medulloblastomas, neuroblastomas, tumors of embryonic origin, astrocytomas, astroblastomas, ependyomas, oligodendrogliomas, plexus tumors, neuroepitheliomas, epiphyseal tumors, ependymoblastomas, malignant meningiomas, sarcomatoses, malignant melanomas, schwannomas);

immune system disorders, in particular autoimmune diseases: psoriasis, lupus erythematosus, connective tissue diseases or connectivitis, Sjögren's syndrome, ankylosing spondylarthritis, undifferentiated spondylarthritis, Behcet's disease, hemolytic autoimmune anemia, multiple sclerosis, amyotrophic lateral sclerosis, amyloses, transplant rejection, diseases affecting the plasmocyte line;

allergic diseases: immediate or delayed hypersensitivity, allergic rhinitis or conjunctivitis, contact dermatitis;

parasitic, viral or bacterial infectious diseases: AIDS, meningitis;

inflammatory diseases, in particular articular diseases: arthritis, rheumatoid arthritis, osteo arthritis, spondylitis, gout, vasculitis, Crohn's disease, irritable bowel syndrome; osteoporosis;

ocular conditions: ocular hypertension, glaucoma;

pulmonary conditions: respiratory tract diseases, bronchospasms, coughs, asthma, chronic bronchitis, chronic respiratory tract obstruction, emphysema;

gastrointestinal diseases: irritable bowel syndrome, intestinal inflammatory disorders, ulcers, diarrhea;

urinary incontinence and bladder inflammation.

The use of the compounds according to the invention for preparing a medicinal product for use in the treatment of the pathologies mentioned above is an integral part of the invention.

The use of the following compounds for preparing a medicinal product for use in the treatment of the pathologies mentioned above is also an integral part of the invention:

2,2,2-trifluoroethyl benzylcarbamate;
2,2,2-trifluoroethyl 4-methoxybenzylcarbamate;
4-nitrophenyl 2-[4-phenylmethoxy)phenyl]ethylcarbamate,
4-chloro-2-nitrophenyl 2-(4-chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-diimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate.

A subject of the invention is also medicinal products which comprise a compound of formula (I), or a salt, or else a hydrate or a solvate, that is pharmaceutically acceptable, of the compound of formula (I). These medicinal products find their use in therapeutics, in particular in the treatment of the pathologies mentioned above.

A subject of the invention is also medicinal products which comprise a compound chosen from the list of compounds below, or a salt, or else a hydrate or a solvate, that is pharmaceutically acceptable, of this compound:

2,2,2-trifluoroethyl benzylcarbamate;
2,2,2-trifluoroethyl 4-methoxybenzylcarbamate;
4-nitrophenyl 2-[4-phenylmethoxy)phenyl]ethylcarbamate,
4-chloro-2-nitrophenyl 2-(4-chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-diimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate.

These medicinal products find their use in therapeutics, in particular in the treatment of the pathologies mentioned above.

According to another of its aspects, the present invention relates to pharmaceutical compositions containing, as active ingredient, at least one compound according to the invention. These pharmaceutical compositions contain an effective dose of a compound according to the invention, or a salt, or a hydrate, or a solvate, that is pharmaceutically acceptable, of said compound, and, optionally, one or more excipients that are pharmaceutically acceptable.

According to another of its aspects, the present invention relates to pharmaceutical compositions containing, as active ingredient, at least one compound chosen from the list of compounds below. These pharmaceutical compositions contain an effective dose of a compound chosen from the list of compounds below, or a salt, or a hydrate, or a solvate, that is pharmaceutically acceptable, of said compound, and, optionally, one or more excipients that are pharmaceutically acceptable:

2,2,2-trifluoroethyl benzylcarbamate;
2,2,2-trifluoroethyl 4-methoxybenzylcarbamate;
4-nitrophenyl 2-[4-phenylmethoxy)phenyl]ethylcarbamate,
4-chloro-2-nitrophenyl 2-(4-chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-diimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate.

Said excipients are chosen, according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active ingredient of formula (I) above or one of the compounds below:

2,2,2-trifluoroethyl benzylcarbamate;
2,2,2-trifluoroethyl 4-methoxybenzylcarbamate;
4-nitrophenyl 2-[4-phenylmethoxy)phenyl]ethylcarbamate,
4-chloro-2-nitrophenyl 2-(4-chlorophenyl)ethylcarbamate;
4-nitrophenyl 2-(3,4-dimethoxyphenyl)ethylcarbamate;
phenyl 2-(3,4-dimethoxyphenyl)ethylcarbamate;
4-cyanophenyl 2-(4-methylphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;

4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-ethyl-5,7-dimethyl-3H-imidazo-[4,5-b]pyridin-3-yl)phenyl]ethylcarbamate;
phenyl 2-[4-(2-amino-4-thiazolyl)phenyl]ethylcarbamate;
2,3,4,5,6-pentafluorophenyl 4-bromobenzylcarbamate;

or its possible salt, solvate or hydrate, can be administered in unit administration form as a mixture with conventional pharmaceutical excipients, to animals and to human beings for the prophylaxis or the treatment of the disorders or of the diseases above. Suitable unit administration forms comprise oral administration forms such as tablets, soft or hard gelatin capsules, powders, granules, chewing gums and oral solutions or suspensions, sublingual, buccal, intratracheal, intraocular and intranasal administration forms, forms for administration by inhalation, subcutaneous, intramuscular or intravenous administration forms, and rectal or vaginal administration forms. For topical application, the compounds according to the invention can be used in creams, ointments or lotions.

By way of example, a unit administration form of a compound according to the invention in tablet form can comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Said unit forms contain doses so as to allow a daily administration of 0.01 to 20 mg of active ingredient per kg of bodyweight, according to the pharmaceutical form.

There may be specific cases where higher or lower doses are appropriate, such doses are also part of the invention. According to the usual practice, the dosage suitable for each patient is determined by the physician according to the method of administration, and the weight and response to said patient.

According to another of its aspects, the invention also relates to a method of treatment of the pathologies indicated above, which comprises the administration of an effective dose of a compound according to the invention, of one of its salts that are pharmaceutically acceptable, or of a solvate or a hydrate of said compound.

What is claimed is:

1. A compound of the formula (I):

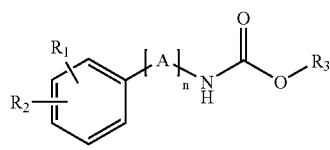

(I)

in which
n represents an integer between 1 and 6;
A is a group X;
X represents a $C_{1-2}$-alkylene group optionally substituted with one or more $C_{1-12}$-alkyl, $C_{3-7}$-cycloalkyl or $C_{3-7}$-cycloalkyl-$C_{1-6}$-alkylene groups;

$R_1$ represents a hydrogen atom, a halogen atom, or a hydroxyl, cyano, nitro, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group;

$R_2$ represents a hydrogen atom, a halogen atom, or a cyano, nitro, hydroxyl, $C_{1-3}$-alkyl, $C_{1-3}$-alkoxy, $C_{1-3}$-thioalkyl, $C_{1-3}$-fluoroalkyl, $C_{1-3}$-fluoroalkoxy or $C_{1-3}$-fluorothioalkyl group, or a group chosen from a phenyl, naphthalenyl biphenyl, phenylethylenyl, naphthylethylenyl, phenyloxy, phenylthio, phenylsulfonyl, benzoyl phenylmethoxy, phenylethoxy, phenylpropoxy, naphthalenyloxy naphthalenylmethoxy, naphthalenylethoxy, and naphthalenylpropoxy, and optionally substituted with one or more substituents chosen from a halogen atom, and the following groups: hydroxyl, cyano, nitro, $C_{1-4}$-alkyl, $C_{1-4}$-alkoxy, $C_{1-4}$-thioalkyl, $C_{1-3}$-fluoroalkyl, $C_{1-3}$-fluoroalkoxy, $C_{1-3}$-fluorothioalkyl, phenyloxy, benzyloxy, piperidyl, pyrrolidinyl, morpholinyl, $NH_2$, $NHR_6$, $NR_6R_7$, $NHCOR_6$, $COR_6$, $CO_2R_6$, $SO_2R_6$, —O—($C_{1-3}$-alkylene)-O—, 4-piperazinyl optionally substituted with a $C_{1-3}$-alkyl or with a benzyl;

$R_3$ represents either a 2,2,2-trifluoroethyl group, or a phenyl group optionally substituted with one or more halogen atoms or cyano, nitro, $C_{1-3}$-alkyl, $C_{1-3}$-alkoxy, trifluoromethyl or trifluoromethoxy groups, and $R_6$ and $R_7$ represent, independently of one another, a $C_{1-3}$-alkyl group or a phenyl;

with the proviso that:
when $R_3$ represents a 2,2,2-trifluoroethyl group and the group -[A]$_n$- represents a —$CH_2$— group, then $R_1$ is other than a hydrogen atom or a methoxy group; and
when $R_3$ represents an optionally substituted phenyl group and the group -[A]$_n$- represents a —$CH_2$—, —$CH_2CH_2$—, —$CH(CH_3)$— or —$CH(CH_3)$—$CH_2$— group, then $R_1$ is other than a hydrogen or chlorine atom or a methyl or methoxy group and $R_2$ is other than a hydrogen atom; and wherein said compound is in the form of a base, or an addition salt with an acid.

2. A process for preparing a compound of formula (I)

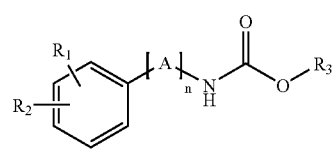

(I)

in which $R_1$, $R_2$, $R_3$, A and n are as defined according to claim 1, comprising the step of:
reacting an amine of formula (II)

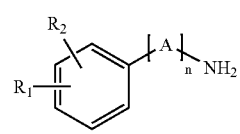

(II)

in which $R_1$, $R_2$, n and A are as defined in formula (I), with a carbonate of formula (III)

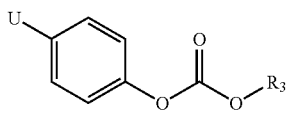

in which U represents a hydrogen atom or a nitro group and $R_3$ is as defined in formula (I).

3. A process for preparing a compound of formula (I)

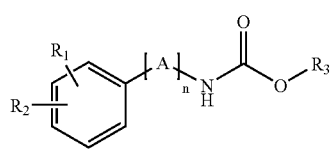

in which
$R_1$, $R_2$, A and n are as defined according to claim 1, and
$R_3$ represents a phenyl group optionally substituted with one or more halogen atoms, or cyano, nitro, $C_{1-3}$-alkyl, $C_{1-3}$-alkoxy, trifluoromethyl or trifluoromethoxy groups, comprising the step of:
reacting an amine of general formula (II)

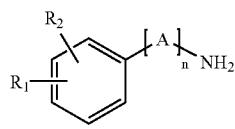

in which $R_1$, $R_2$, n and A are as defined in general formula (I), with an aryl chloroformate of general formula (IIIa)

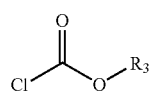

in which $R_3$ represents a phenyl group optionally substituted with one or more halogen atoms, or cyano, nitro, $C_{1-3}$-alkyl, $C_{1-3}$-alkoxy, trifluoromethyl or trifluoromethoxy groups.

4. A pharmaceutical composition comprising at least one compound of formula (I) as claimed in claim 1, in the form of a base, or a pharmaceutically acceptable salt, in combination with one or more pharmaceutically acceptable excipients.

5. The pharmaceutical composition as claimed in claim 4, wherein compound of formula (I) is selected from the group consisting of:
2,2,2-trifluoroethyl benzylcarbamate;
2,2,2-trifluoroethyl 4-methoxybenzylcarbamate;
4-nitrophenyl 2-[4-(phenylmethoxy)phenyl]ethylcarbamate;
4-chloro-2-nitrophenyl 2-(4-(chlorophenyl)ethylcarbamate;
phenyl 2-(3,4-dimethoxyphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-amino-4-thiazolyl)phenyl]ethylcarbamate; and
2,3,4,5,6-pentafluorophenyl 4--bromobenzy-lcarbamate;
in the form of a base, or a pharmaceutically acceptable salt, hydrate or a solvate thereof.

6. The compound of formula (I) as claimed in claim 1, in the form of a base, or a pharmaceutically acceptable salt thereof.

7. The compound of formula (I) as claimed in claim 1, which is chosen from the following compounds:
2,2,2-trifluoroethyl benzylcarbamate;
2,2,2-trifluoroethyl 4-methoxybenzylcarbamate;
4-nitrophenyl 2-[4-(phenylmethoxy)phenyl]ethylcarbamate;
4-chloro-2-nitrophenyl 2-(4-(chlorophenyl)ethylcarbamate;
phenyl 2-(3,4-dimethoxyphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;
4-nitrophenyl 2-(4-hydroxyphenyl)ethylcarbamate;
phenyl 2-[4-(2-amino-4-thiazolyl)phenyl]ethylcarbamate; and
2,3,4,5,6-pentafluorophenyl 4-bromobenzylcarbamate;
in the form of a base, or a pharmaceutically acceptable salt thereof.

8. A method of treatment of a disease in a patient comprising administering to said patient a therapeutically effective amount of a compound of formula (I) as claimed in claim 1, in the form of a base, or a pharmaceutically acceptable salt, wherein said disease is selected from the group consisting of acute or chronic pain, vomiting, nausea, an eating disorder, a sleep disorder, and renal ischemia.

9. The method as claimed in claim 8, wherein the compound of formula (I) is chosen from the following compounds:
2,2,2-trifluoroethyl benzylcarbamate;
2,2,2-trifluoroethyl 4-methoxybenzylcarbamate;
4-nitrophenyl 2-[4-(phenylmethoxy)phenyl]ethyl-carbamate;
4-chloro-2-nitrophenyl 2-(4-(chlorophenyl)ethylcarbamate;
phenyl 2-(3,4-dimethoxyphenyl)ethylcarbamate;
2,4,5-trichlorophenyl 2-(4-chlorophenyl)ethylcarbamate;
phenyl 4-chlorobenzylcarbamate;
phenyl 4-methoxybenzylcarbamate;
4-fluorophenyl 2-(4-methoxyphenyl)ethylcarbamate;
phenyl 3-nitrobenzylcarbamate;
4-cyanophenyl 4-methoxybenzylcarbamate;
phenyl 3-chlorobenzylcarbamate;
phenyl 3,4-dichlorobenzylcarbamate;

4-nitrophenyl 2-(4-hydroxyphenyl)ethylcarbamate;
phenyl 2-[4-(2-amino-4-thiazolyl)phenyl]ethylcarbamate; and
2,3,4,5,6-pentafluorophenyl 4--bromobenzyl-carbamate;
in the form of a base, or a pharmaceutically acceptable salt, hydrate or a solvate thereof.

10. The method as claimed in claim 8 wherein the disease is acute or chronic pain.

11. The method as claimed in claim 8 wherein the disease is vomiting, nausea, or an eating disorder.

12. The method as claimed in claim 8 wherein the disease is a sleep disorder.

13. The method as claimed in claim 8 wherein the disease is renal ischemia.

14. The method as claimed in claim 9 wherein the disease is acute or chronic pain.

15. The method as claimed in claim 9 wherein the disease is vomiting, nausea or an eating disorder.

16. The method as claimed in claim 9 wherein the disease is a sleep disorder.

17. The method as claimed in claim 9 wherein the disease is renal ischemia.

* * * * *

UNITED STATES PATENT AND TRADEMARK OFFICE
CERTIFICATE OF CORRECTION

PATENT NO. : 7,696,374 B2
APPLICATION NO. : 11/395942
DATED : April 13, 2010
INVENTOR(S) : Ahmed Abouabdellah et al.

Page 1 of 2

It is certified that error appears in the above-identified patent and that said Letters Patent is hereby corrected as shown below:

On the Title page, Item (54) in "Title" and Col. 1 line 1, delete "ARYLALKLCARBAMATE" and insert -- ARYLALKYLCARBAMATE --, therefor.

On the Title page, Item (56), under "Other Publications", line 5, delete "Recepteros" and insert -- Receptors --, therefor.

On the Title page, Item (56), under "Other Publications", line 5, delete "Cardivascular" and insert -- Cardiovascular --, therefor.

On the Title page, 2nd Col. Item (Primary Examiner) line 1, delete "Nazaril" and insert -- Nazario --, therefor.

On Title page 2, Item (56) under "Other Publications", line 16, delete "Transamission" and insert -- Transmission --, therefor.

In column 1, line 1, delete "ARYLALKLCARBAMATE" and insert -- ARYLALKYLCARBAMATE --, therefor.

In column 4, line 23, delete "naphthalenyl-propoxy," and insert -- naphthalenylpropoxy, --, therefor.

In column 7, line 2, delete "$C_{1-1-2}$-alkyl," and insert -- $C_{1-12}$-alkyl, --, therefor.

In column 12, line 31, delete "$NHR_6$." and insert -- $NHR_6$, --, therefor.

In column 16, line 1, delete "$^1$HNMR" and insert -- $^1$H NMR --, therefor.

In column 16, line 1, delete "$^1$HNMR" and insert -- $^1$H NMR --, therefor.

In column 22, line 9, in claim 1, after "naphthalenyl" insert -- , --.

Signed and Sealed this
Thirty-first Day of May, 2011

David J. Kappos
*Director of the United States Patent and Trademark Office*

CERTIFICATE OF CORRECTION (continued)
U.S. Pat. No. 7,696,374 B2

In column 22, line 11, in claim 1, after "benzoyl" insert -- , --.

In column 22, line 12, in claim 1, after "naphthalenyloxy" insert -- , --.

In column 24, line 11, in claim 5, delete "4--" and insert -- 4- --, therefor.

In column 24, line 11, in claim 5, delete "bromobenzy-lcarbamate;" and insert -- bromobenzylcarbamate; --, therefor.

In column 24, line 12-13, in claim 5, after "salt" delete ", hydrate or a solvate".

In column 24, line 54-55, in claim 9, delete "ethyl-carbamate;" and insert -- ethylcarbamate; --, therefor.

In column 25, line 4, in claim 9, delete "4--" and insert -- 4- --, therefor.

In column 25, line 4, in claim 9, delete "bromobenzyl-carbamate;" and insert -- bromobenzylcarbamate; --, therefor.

In column 25, line 5-6, in claim 9, after "salt" delete ", hydrate or a solvate".